United States Patent [19]

Tsuboi

[11] Patent Number: 5,214,960
[45] Date of Patent: Jun. 1, 1993

[54] METHOD AND APPARATUS FOR DETECTING DEFECTS IN AN OBJECT BY VIBRATING THE OBJECT IN A PLURALITY OF POSITIONS

[75] Inventor: Kiyoshi Tsuboi, Tokyo, Japan

[73] Assignee: Honda Giken Kogyo Kabushiki Kaisha, Tokyo, Japan

[21] Appl. No.: 680,111

[22] Filed: Apr. 3, 1991

[51] Int. Cl.$^5$ .............................................. G01N 29/12
[52] U.S. Cl. ........................................ 73/579; 73/646; 364/508
[58] Field of Search ................. 73/579, 582, 583, 592, 73/602, 645, 646, 658, 659; 364/508

[56] References Cited

U.S. PATENT DOCUMENTS 3,916,699  11/1975  Moran et al. .......................... 73/592
4,519,245   5/1985  Evans ..................................... 73/579
4,829,823   5/1989  Michel .................................... 73/579

FOREIGN PATENT DOCUMENTS 0102176  7/1984  European Pat. Off. .
1539927  2/1979  United Kingdom .
1545505  5/1979  United Kingdom .

Primary Examiner—Hezron E. Williams
Assistant Examiner—Rose M. Finley

[57] ABSTRACT

A test object such as an engine cylinder is inspected for any defect such as a crack, a blowhole, a cavity, or the like by applying vibration to the test object at two different positions on a side thereof. While the test object is vibrating, signals indicative of the vibration of the test object are detected. From the detected signals, there are produced a signal indicative of a natural vibration of the test object and a signal indicative of a defect-induced vibration of the test object. The signal indicative of a natural vibration and the signal indicative of a defect-induced vibration are compared to determine whether there is a defect in the test object.

24 Claims, 14 Drawing Sheets

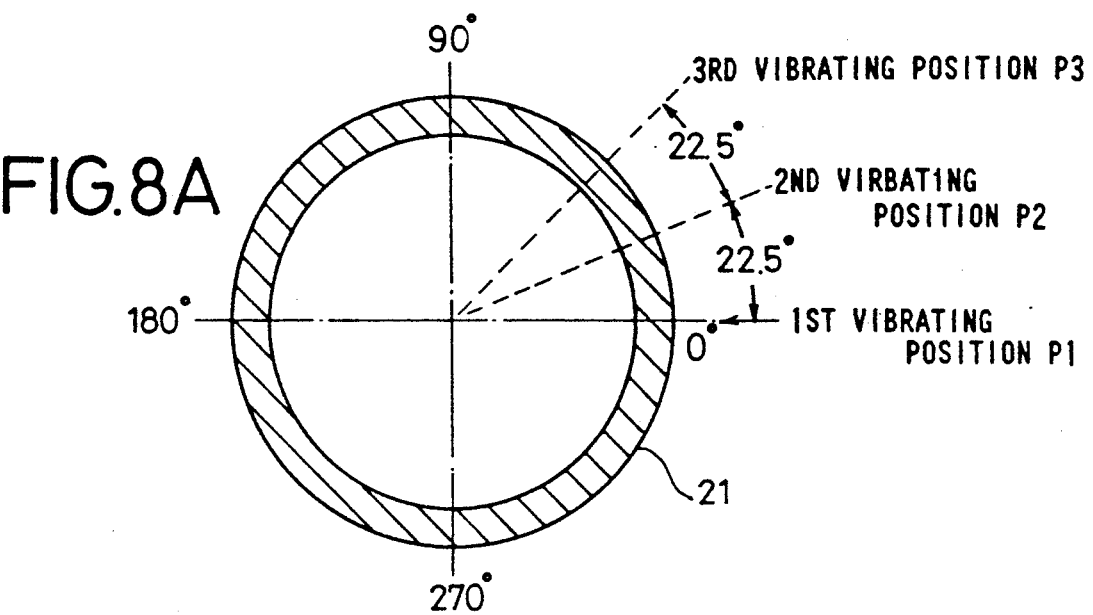
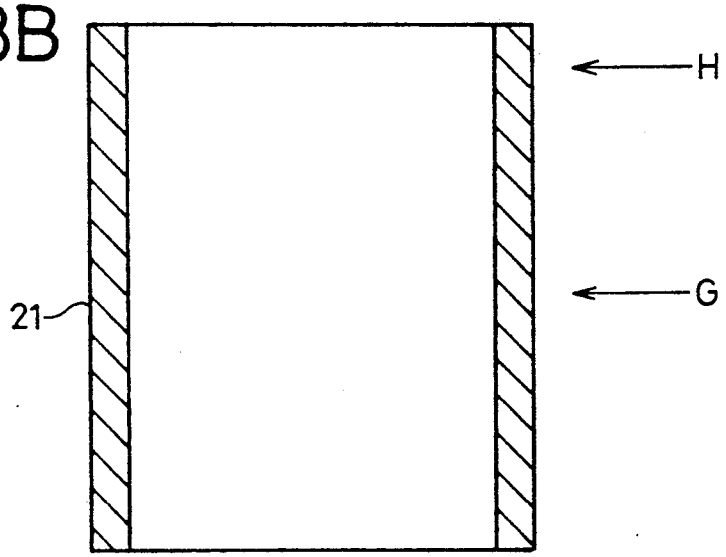

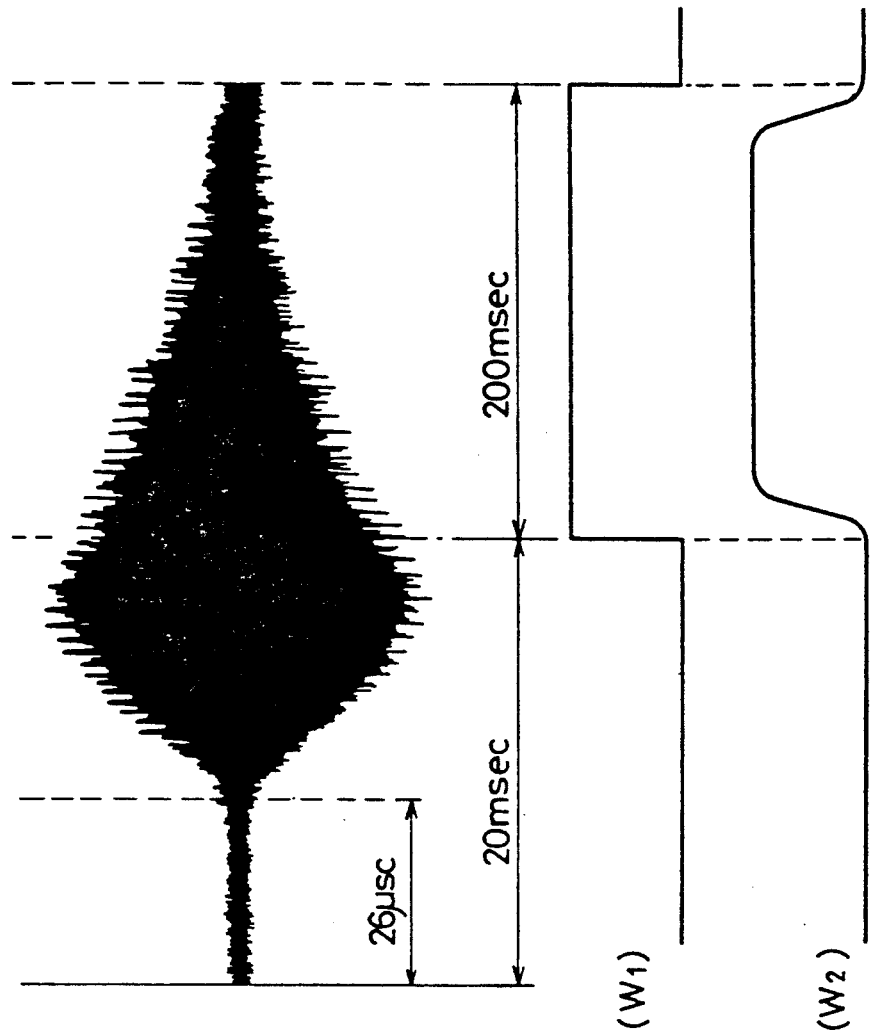

METHOD AND APPARATUS FOR DETECTING DEFECTS IN AN OBJECT BY VIBRATING THE OBJECT IN A PLURALITY OF POSITIONS

BACKGROUND OF THE INVENTION

1. Field of the Invention

The present invention relates to a method of and an apparatus for detecting a defect such as a crack, a recess, a cavity, or the like in a test object.

2. Prior Art

Cylinder/piston mechanisms for use in automotive engines may fail to operate properly if cylinders and pistons have defects such as cracks, cavities, recesses, or the like. Parts with such cracks, cavities, or recesses should preferably be sorted out on parts production lines before they are assembled into engines.

Various nondestructive testing methods are known for detecting these defects in engine components. For example, engine component deficiencies have been detected by an ultrasonic echo method, an acoustic emission method which detects a sonic energy wave caused when a crack is produced in a component, a CCD camera image observation method, a radiographic method, a visual-optical method using a color check, and an eddy current method, among others.

However, the above testing methods have been problematic for the following reasons:

The ultrasonic echo method uses a transducer or sensor for transmitting and receiving ultrasonic energy into and from a test object. In use, the sensor is held in contact with the test object. Since, however, the ultrasonic energy is propagated linearly through the test object, only the area of the test object which is in contact with the sensor can be tested. The waveform of the ultrasonic energy received from the test object tends to vary due to reflections caused by inadequate coupling between the sensor and the test object or due to slight changes in the angle of the sensor with respect to the test object. Consequently, it is not easy to achieve proper determination of defects in test objects.

The acoustic emission method also employs a sensor held in contact with a test object. Inasmuch as a crack is detected on the basis of an acoustic emission signal produced when the crack is caused, a crack can be detected only while the crack is being developed. Difficulty arises in this testing method unless the crack to be detected is increasing in a test object.

The CCD camera image observation method is liable to detect discolored spots and patterns other than real defects and is not effective to detect cavities known as blowholes in castings.

The radiographic method allows the operator to make a visual inspection of the internal structure of a test object. However, it is cumbersome to regulate the dose of X-rays to be applied to a test object. A crack in a test object may not be observed if the dose of applied X-rays is not properly regulated. Since the radiographic method cannot efficiently inspect all test objects that need to be tested, it is not suitable for inspection on production lines.

In the eddy-current method, a test object is rotated at high speed, and a sensor has to be positioned closely to and uniformly moved with respect to the test object. If the test object has surface irregularities, however, measurements are difficult to achieve because the sensor cannot be positioned near the test object.

SUMMARY OF THE INVENTION

It is an object of the present invention to provide a method of and an apparatus for easily and reliably detecting a defect such as a crack, a cavity, a recess, or the like in a test object out of contact therewith.

Another object of the present invention is to provide a method of and an apparatus for detecting a defect such as a crack, a cavity, a recess, or the like in a test object with a sensor, without concern over waveform changes which would otherwise result from reflections caused by inadequate coupling between the sensor and the test object or from slight changes in the angle of the sensor with respect to the test object.

Still another object of the present invention is to provide a method of and an apparatus for detecting a crack in a test object without the crack size being increased and also for easily detecting a blowhole in a casting.

Yet another object of the present invention is to provide a method of and an apparatus for detecting defects in all test objects that need to be inspected and for inspecting test objects on production lines for defects.

According to the present invention, there is provided a method of detecting a defect in a test object, comprising applying vibration to a three-dimensional test object in at least two positions on a side thereof to vibrate the test object, detecting signals indicative of the vibration of the test object, which signals are produced when the test object is vibrated at the at least two positions, detecting, based on the signals, a signal indicative of a natural vibration of the test object and a signal indicative of a defect-induced vibration of the test object, and comparing the signal indicative of the natural vibration and the signal indicative of the defect-induced vibration, thereby to determine whether there is a defect in the test object.

According to the present invention, there is also provided an apparatus for detecting a defect in a test object, comprising vibrating means for vibrating a test object in a plurality of positions, detecting means for detecting vibration of the test object and converting the detected vibration into an electric signal, and determining mean for determining whether there is a defect in the test object from a signal from the detecting means which is indicative of a natural vibration of the test object and a signal from the detecting means which is indicative of a defect-induced vibration of the test object.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIGS. 8A and 8B are transverse and longitudinal cross-sectional views, respectively, of the test object, showing positions where vibration is applied to the test object for the detection of a defect in the test object., FIGS. 9A, 9B, and 9C are diagrams showing the waveforms of natural vibrations of the test object, an extracting window, and an emphasizing window;

DETAILED DESCRIPTION OF THE PREFERRED EMBODIMENT

A method of detecting a defect in a test object according to the present invention is basically characterized by vibrating the test object and detecting whether there is a defect in the test object or not and the position of a defect, if any, in the test object, based on the vibration of the test object. First, the fundamental principles of the defect detecting method will be described below.

For example, a cast hollow cylindrical component for use as an automotive engine cylinder will hereinafter be employed as a test object.

Figure 1A:
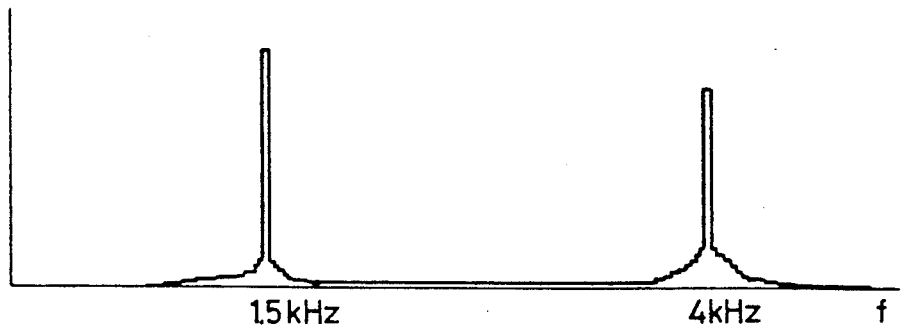
FIGS. 1A through 1D are diagrams of spectral waveforms illustrating the principles of a method of detecting defects according to the present invention.

The cylindrical component is vibrated by application of an impact thereto, and the vibration of the cylindrical component is picked up by a displacement meter or a vibration sensor having sharp directivity. If the cylindrical component does not have any defects such as cracks, cavities, recesses, or the like, then a spectral analysis of the natural vibration of the cylindrical component produces a spectrum having a first-order energy peak, a second-order energy peak, and so on, as shown in FIG. 1A. The energy peaks are produced at fixed frequencies depending on the shape and size of the cylindrical component which is free of any defects.

Figure 2:
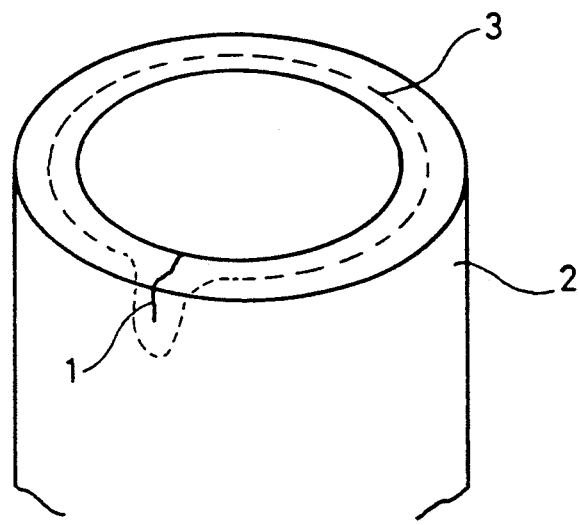
FIG. 2 is a fragmentary perspective view of a cylindrical test object, illustrating the principles of the defect detecting method according to the present invention.

If the cylindrical component has a crack extending through the cylindrical wall thereof, then two separate energy peaks are observed in each of odd-numbered-order spectral regions according to a spectral analysis of the natural vibration. The reason for two separate energy peaks in the odd-numbered-order spectral regions is as follows: As shown in FIG. 2, if there is a crack 1 extending through the cylindrical wall of a cylinder 2, then a vibratory wave propagated in the cylindrical wall of the cylinder 1 does not pass through the crack 1, but rather bypasses the crack 1 axially of the cylindrical component as indicated by the dotted line in FIG. 2. Since the vibratory wave is propagated along a longer path, a crack-induced spectral peak is produced at a frequency lower than the fundamental natural frequency of the cylinder 2.

Figure 1B:
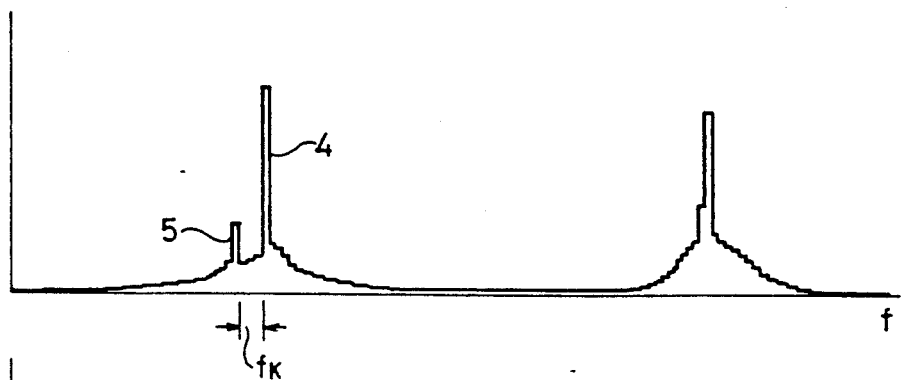

Therefore, if the cylindrical component has a crack in the cylindrical wall thereof, as shown in FIG. 1B, a crack-induced spectral energy peak 5 appears which is lower in frequency than a first-order spectral energy peak 4 of fundamental natural vibration. The sum of the energies of the peaks 4, 5 is equal to the energy of the first-order spectral peak which would be produced if the cylindrical component had no crack, as shown in FIG. 1A. In FIG 1B, there is only one energy peak in the second-order spectral region.

The magnitude (length) of the crack is proportional to the frequency difference fK between the two spectral energy peaks 4, 5. The magnitude of the crack means the volume of the crack. If the test object is cylindrical, then the wall thickness thereof is constant and the width of the crack is negligibly small, and hence the magnitude of the crack is actually representative of the length thereof. It was confirmed with the cylindrical component referred to above that a frequency difference fK=5 Hz indicated a crack having a length of 4 mm.

Figure 3:
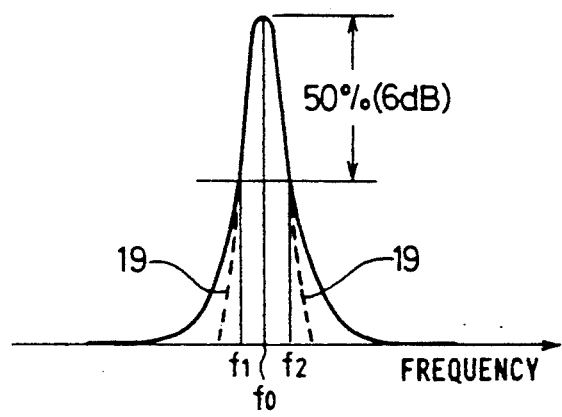
FIG. 3 is a diagram illustrative of Q or a value of sharpness of resonance or frequency selectivity with respect to frequencies at the time the cylindrical test object is vibrated.

In the case where any crack which is present is very small, the Q ($(f1-f2)/f0$, see FIG. 3) of the odd-numbered-order spectral regions is increased, resulting in a widened waveform. This appears to result from the fact that the spectral energy peak produced by the fundamental natural vibration and the spectral energy peak produced by the vibration bypassing the crack are observed as being coupled together.

Consequently, whether there is a crack or not can be ascertained by detecting the magnitude of the Q of an odd-numbered-order spectral region, e.g., the first-order spectral region.

Figure 1C:
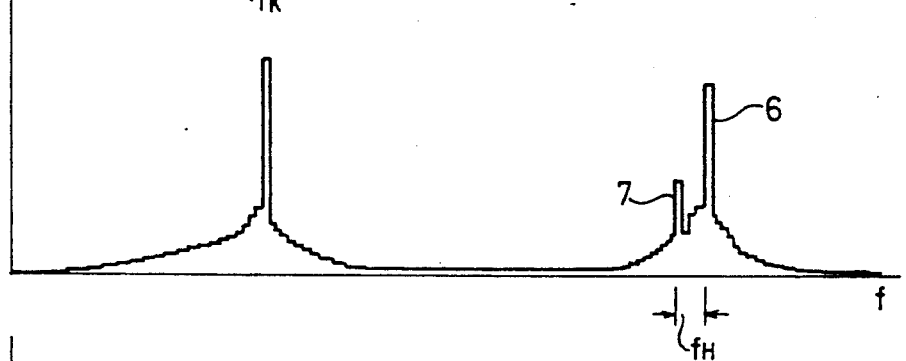

If the cylindrical component has a trapped defect such as a blowhole or a cavity which does not extend through the cylindrical wall and does not have a crack extending through the cylindrical wall, there are no two separate energy peaks in each of the odd-numbered-order spectral regions as shown in FIG. 1C. Therefore, such a trapped defect cannot be detected simply by examining the odd-numbered-order spectral regions. This is because the first-order vibration does not bypass such a trapped defect axially in the cylindrical wall.

However, since the vibratory wall nevertheless bypass a trapped defect transversely or radially in the cylindrical wall, there are observed two separate spectral energy peaks in an even-numbered-order spectral region, e.g., a second-order spectral region. FIG. 1C shows a spectrum of the natural vibration of a cylindrical component having a trapped defect such as a blowhole or cavity. The spectrum shown in FIG. 1C indicates a spectral energy peak 6 produced by the fundamental natural vibration and a spectral energy peak 7 produced by the vibration bypassing a trapped defect. The sum of the energies of the peaks 6, 7 is equal to the energy of the second-order spectral peak which would be produced if the cylindrical component had no trapped crack. The spectral energy peak produced by the vibration bypassing the trapped defect appears at a frequency lower than the natural frequency in the second-order spectral region.

The magnitude of the crack is proportional to the frequency difference fk between the two spectral energy peaks 6, 7.

Figure 1D:
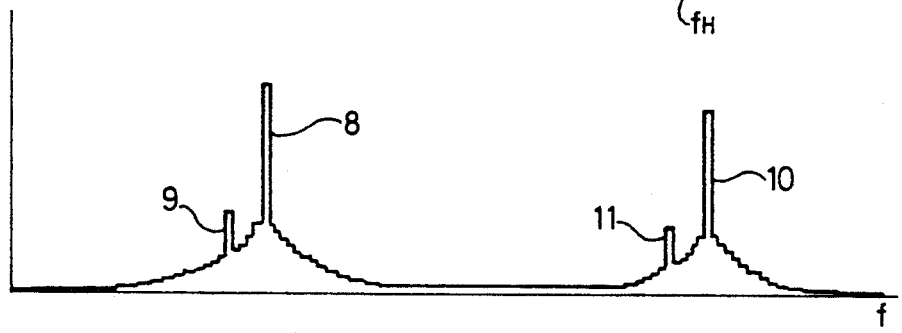

If the cylindrical component has both a through defect and a trapped defect, such as a crack and a cavity, respectively, each of first- and second-order spectral regions of a spectrum of fundamental natural vibration includes two spectral energy peaks, as shown in FIG. 1D. In the first-order spectral region, a spectral energy peak 8 is caused by the fundamental natural vibration of the cylindrical component, and a spectral energy peak 9, which is lower in frequency than the spectral energy peak 8, is induced by a through defect such as a crack in the cylindrical component. In the second-order spectral region, a spectral energy peak 10 is caused by the fundamental natural vibration of the cylindrical component, and a spectral energy peak 11, which is lower in frequency than the spectral energy peak 10, is induced by a trapped defect such as a cavity in the cylindrical component Inasmuch as the spectral energy peak 11 induced by the trapped defect is affected by the through defect, the magnitude of the trapped defect is obtained by subtracting the frequency difference fK from the frequency difference fH.

In case a trapped defect such as a blowhole or cavity is very small, the spectral energy peak induced thereby is included in the spectral energy peak caused by the fundamental natural vibration in the second-order spectral region. Such a small trapped defect can however be detected by determining the magnitude of the Q because the Q is increased by the trapped defect.

In carrying out the defect detecting method according to the present invention, it is necessary to apply vibration to a test object. Spectral energy peaks caused by fundamental natural vibrations of a test object and spectral energy peaks caused by vibrations induced by a defect in the test object vary depending on the position where the vibration is applied to the test object, with respect to the position of the defect in the test object. If the test object is vibrated only at one position, then the following problem arises:

As described above, when the test object is vibrated, the sum of the energy peak of the fundamental natural vibration and the energy peak of the vibration induced by the defect remains constant irrespective of the position where the vibration is applied to the test object. The magnitudes of the fundamental natural vibration and the vibration induced by the defect vary dependent on the position where the vibration is applied to the test object, with respect to the position of the defect in the test object. Therefore, the ratio of the energy peaks of the fundamental natural vibration and the defect-induced vibration varies depending on the position where the vibration is applied to the test object.

Figure 4:
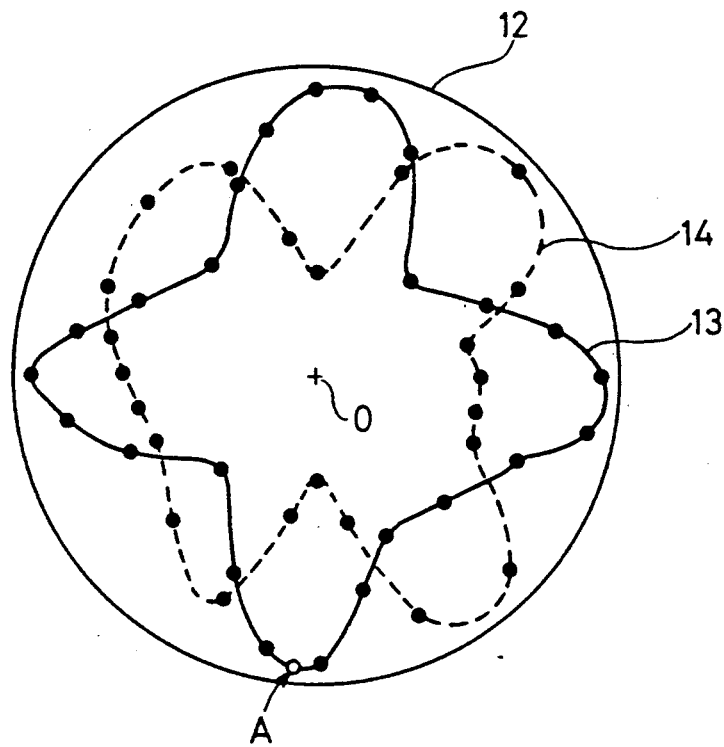
FIG. 4 is a diagram showing curves representing the locus of first-order spectra energy peaks which are caused by the fundamental natural vibration of the cylindrical test object and the locus of first-order spectral energy peaks which are induced by a defect in the cylindrical test object.

For example, how spectral energy peaks vary when a cylindrical test object is vibrated by primary vibration will be considered below. As shown in FIG. 4 the vibration is applied to the test object at a position A on the circumferential surface thereof, and spectral energy peaks of fundamental natural vibrations in the first-order spectral region are plotted as magnitudes from the center O of the cylindrical test object at various angular positions along the entire circumferential surface. If the test object is free of defects (cracks), then the locus of the plotted energy peaks is represented by a curve 13. The locus of energy peaks plotted when they are induced by a defect in the test object is represented by a curve 14. At some angular positions, the spectral energy peaks produced by the fundamental natural vibration are larger and the spectral energy peaks induced by the defect are smaller. At some other angular positions, the spectral energy peaks produced by the fundamental natural vibration are smaller and the spectral energy peaks induced by the defect are larger. The curves 13, 14 repeat substantially sinusoidal patterns at each angular interval of 90° and are 45° out of phase with each other.

The curve 13 or 14 repeats its pattern at each angular interval of 90° because when the cylindrical test object is vibrated, if there are no defects, the first-order vibration of the test object repeats between a condition indicated by the dot-and-dash line 15 and a condition indicated by the two-dot-and-dash line 16, as shown in FIG. 15. At a position B which is 180° spaced from the position A, the test object vibrates in exactly the same pattern as the pattern in the position A. At positions C, D which are 90° spaced from the position A, the test object vibrates in a pattern opposite to the pattern in the position A. Therefore, the test object vibrates as shown in FIG. 5 irrespective of whether it is vibrated in any of the 90°-spaced positions A, B, C, D.

Figure 5:
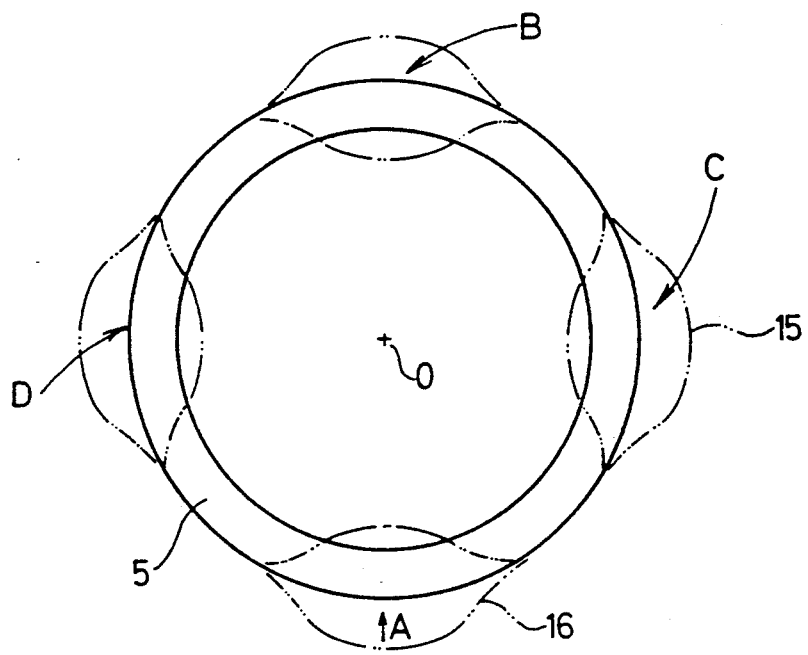
FIG. 5 is a diagram showing the manner in which the primary vibration of the test object repeats between different conditions.

As shown in FIG. 5, the energy peaks induced by the defect are smaller at those angular positions where the energy peaks caused by the fundamental natural vibration are larger, and vice versa. In order to determine these two types of energy peaks in a short period of time in the event that the test object has a defect, the test object may be vibrated in such a position as to equalize the amplitudes of the energy peaks.

However, since the position of any defect in a test object is unknown, it is impossible to determine, in advance, the position where the test object is to be vibrated, with respect to the position of the defect. If the test object is vibrated only in one position, the vibration induced by the defect may be too large or the fundamental natural vibration may be too large, depending on that position. In such a case, it would be difficult to distinguish spectral changes due to material differences in the test object from spectral changes due to the presence of a defect in the test object, resulting in a lengthy process for defect detection.

According to the present invention, vibration is applied to a test object at two or more positions which are angularly spaced other than 90°×n (n=1, 2, 3). Even if the fundamental natural vibration or the defect-induced vibration is too large in one of those positions, no such condition occurs in the other positions. When the results of analysis of the vibrations of the test object which is vibrated in those positions are combined with other, the presence or absence of any defect in the test object can easily be determined.

It has been found in accordance with the present invention that when a test object is vibrated at an angular position aligned with a defect in the test object, the energy of defect-induced vibration is minimum and the energy of fundamental natural vibration is maximum. Consequently, the position of a defect, such as a crack which is a through defect, can be detected as an angular position where the difference between the energy peaks of the defect-induced vibration and the fundamental natural vibration. In the test object shown in FIG. 4, there is a crack at the angular position indicated by the arrow A.

Specifically, the test object is vibrated successively in a plurality of angular positions therearound, and the energy peak PK1 of fundamental natural vibration and the energy peak PK2 of crack-induced vibration are determined in each of those angular positions. Then, the position where the difference (PK1−PK2) between the energy peaks PK1, PK2 is maximum can be detected as the position of a crack in the test object.

If a test object has a circular or elliptical cross-sectional shape, as shown in FIG. 4, a crack may possibly be present in any of four 90°-spaced positions where the energy peak of fundamental natural vibration is maximum and the energy peak of crack-induced vibration is minimum. When either one of the locus of the energy peaks of fundamental natural vibration and the locus of the energy peaks of crack-induced vibration is known, the four positions where a crack may possibly exist can be determined.

As described above, each of the loci of the energy peaks shown in FIG. 4 repeats a substantially sinusoidal pattern at each interval of 90°. The loci are distorted because the crack is inclined with respect to the axial direction of the cylindrical test object. If the crack extends parallel to the axial direction of the test object, then the loci repeats a substantially identical pattern at each interval of 90°. The direction in which the crack is bent can be known from the area occupied by the repetitive locus waveform of the crack-induced energy peaks, i.e., the crack is bent toward a greater proportion of the area. In FIG. 4, the crack is bent to the right.

Since the locus of the energy peaks repeats a pattern at each 90° interval, the test object may be vibrated in an angular range of 90°, the locus of energy peaks may be determined in that angular range, and the entire locus along the full circumference of the test object may be estimated from the 90°-range locus for the determination of the position of a crack in the test object.

In order to reproduce a tortuous locus waveform as shown in FIG. 4, values from at least three points are necessary. Since it is known that the same results are produced when the test object is vibrated at 90°-spaced positions, positions which are angularly spaced by 90°, 180°, 270° are not selected, but at least three positions which are angularly spaced by 90°/3 or less for vibrating the test object. In this manner, the locus of energy peaks in an angular range of 90° can be plotted, and the locus in the angular range of 360° fully around the test object can be estimated from the 90°-range locus. From the estimated locus, there can be determined four positions where a crack may possibly be present.

While the first-order vibration has been described above with respect to the detection of a through defect, a trapped defect such as a blowhole or cavity can similarly be detected on the basis of second-order vibration of a test object.

Figure 6:
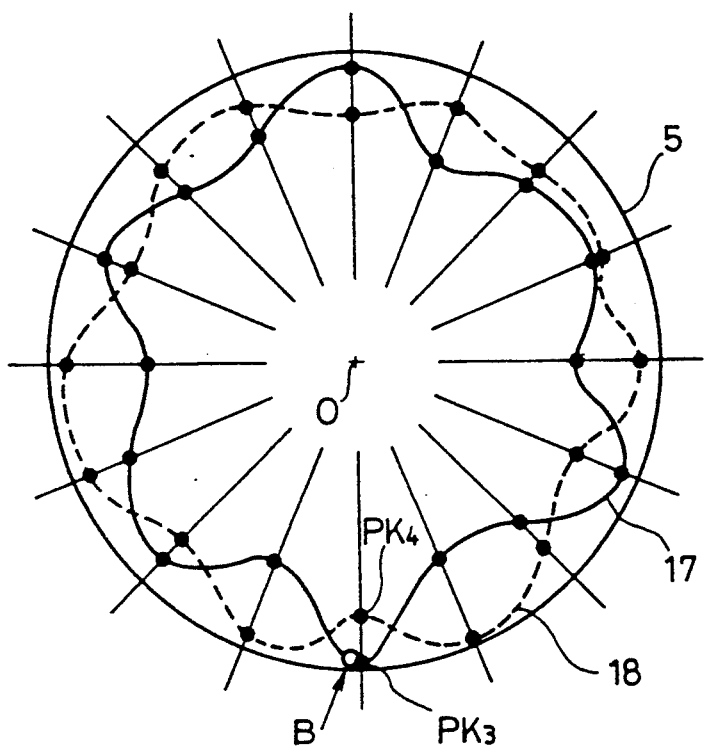
FIG. 6 is a diagram showing curves representing the locus of second-order spectral energy peaks which are caused by the fundamental natural vibration of the cylindrical test object and the locus of second-order spectral energy peaks which are induced by a defect in the cylindrical test object.

FIG. 6 shows a curve 17 representing the locus of spectral energy peaks of a fundamental natural vibration in a second-order spectral region and a curve 18 representing the locus of spectral energy peaks of a defect-induced vibration in the second-order spectral region, when the test object has a trapped defect. The curves 17, 18 repeat substantially sinusoidal patterns at each angular interval of 60°, and are 30° out of phase with each other.

The position where the difference (PK3−PK4) between the energy peak PK3 of a fundamental natural vibration and the energy peak PK4 of a defect-induced vibration is maximum can be detected at the position where the trapped defect exists. In the test object shown in FIG. 6, there is a trapped defect at the angular position indicated by the arrow B.

If a test object has a circular or elliptical cross-sectional shape, since the locus waveforms are repetitive, six positions (360°÷6) where a trapped defect may possibly be present can be determined from a locus in an angular range of at east 60°. Because the results of the analysis of second-order vibrations remain the same when the test object is vibrated at angular positions which are 60° apart, the test object is vibrated in a plurality of angular positions which are not indicated by integral multiples of 60°.

The locus waveforms shown in FIG. 6 may be considered to be repetitive at each interval of 120°. Thus, when the test object is vibrated in angular positions which are spaced by 90°/3 or less, spectral energy peaks produced by vibrating the test object in four or more positions are obtained in an angular interval of 120°, making it possible to estimate and plot the locus waveforms shown in FIG. 6.

Therefore, if a test object is of a circular or elliptical cross-sectional shape, such as a cylindrical shape, the test object is vibrated in three or more positions which are angularly spaced by 90°/3 or less, except integral multiples of 90° and integral multiples of 60°, and spectral energy peaks of fundamental natural vibration o spectral energy peaks of defect-induced vibration are detected in each of the above positions. Positions where a defect may possibly exist in the test object can be determined from the locus of the detected energy peaks in the positions where the test object is vibrated.

Figure 7:
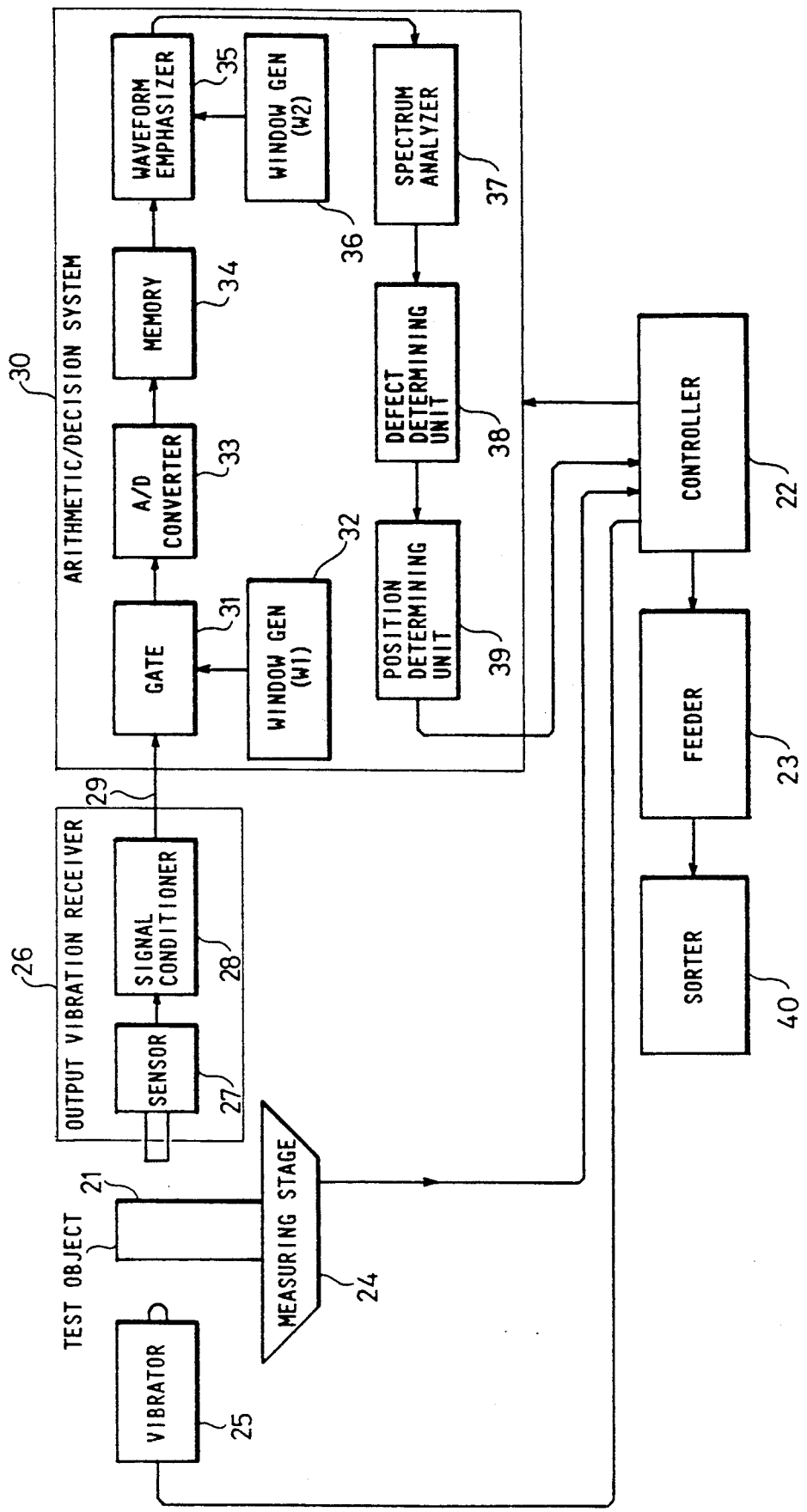
FIG. 7 is a block diagram of an apparatus for carrying out the defect detecting method according to the present invention.

An apparatus for carrying out the defect detecting method according to the present invention is illustrated in FIG. 7. The apparatus shown in FIG. 7 automatically inspects all cylindrical products such as engine cylinders on a production line and sorts acceptable and defective products.

An engine cylinder as a test object 21 is fed along the production line by a feeder 23 which is controlled by a controller 23 which comprises a microcomputer, and placed on a measuring stage 24.

The measuring stage 24 is rotatable about its own axis and may be made of hard rubber, for example. When the test object 21 placed on the measuring stage 24 is detected by a detector (not shown) on the measuring stage 24, for example, the controller 22 actuates a vibrator 25 to vibrate the test object 21. For example, the vibrator 25 comprises a pendulum weight which is brought into hitting engagement with the test object 21 to exert an impulsive force or impact on the test object 21. The pendulum weight may be driven by a cam mechanism or the like, for example, which moves back the pendulum weight off the test object 21 immediately after the pendulum weight has hit the test object 21.

The vibrator 25 impacts the cylindrical test object 21 simultaneously or successively in a plurality of positions on an outer circumferential surface thereof, which are angularly spaced positions except those indicated by integral multiples of 90° and 60° such as 90°, 180°, 270°.

FIGS. 8A and 8B show different positions in which the test object is vibrated by the vibrator 25. In the illustrated embodiment, the vibration is applied to the test object 21 in three successive angular positions. As shown in FIG. 8A, the test object 21 is vibrated at first vibrating position P1 and two further vibrating positions P2, P3 which are angularly spaced 22.5° and 45°, respectively, from the first vibrating position P1. The measuring stage 24 is rotatable in a horizontal plane, and the cylindrical test object 21 is placed thereon with its central axis aligned with the axis about which the measuring stage 24 is rotatable.

First, the test object 21 is vibrated at the first position P1 on its outer circumference by the vibrator 25. Thereafter, the measuring stage 24 is turned through 22.5°, and the test object 21 is vibrated at the second position P2. After the measuring stage 24 is further turned through 22.5°, the test object 21 is vibrated at the third position P3.

The vibration is applied to the test object 21 in an axial region thereof which is displaced off the center of gravity G of the test object 21 (which is theoretically determined from the configuration of the test object 21), e.g., at a position H near the upper end of the test object 21.

When the test object 21 is vibrated in a region off the center of gravity thereof, if the mass (weights) of portions of the test object 21 which are above and below the center of gravity are different from each other (generally, all substances have a different mass), other spectral energy peaks appear in addition to the spectral energy peaks of natural vibration in the first- and second-order spectral regions. The frequencies of the other energy peaks depend on the upper and lower masses of the test object 21. The frequency of the energy peak which depends on the greater mass (e.g., the lower portion of the test object 21) is higher, whereas the frequency of the energy peak which depends on the smaller mass (e.g., the upper portion of the test object 21) is lower.

If the test object 21 has a defect in the upper portion thereof, the energy peak of a defect-induced vibration and the lower-frequency energy peak of a fundamental natural vibration appear as a pair, and if the test object 21 has a defect in the lower portion thereof, the energy peak of a defect-induced vibration and the higher-frequency energy peak of a fundamental natural vibration appear as a pair. Therefore, whether a defect is positioned in the upper or lower portion of the test object 21 can be determined by finding which energy peak of a fundamental natural vibration is accompanied by the defect-induced energy peak. If both energy peaks of a fundamental natural vibration are accompanied by respective defect-induced energy peaks, then the defect is determined to be located in the center of the test object. Whether the test object 21 is hit by the vibrator 25 at its portion above or below the center of gravity G may be determined based on positional information of the vibrator 25 and the measuring stage 24 which is supplied to the controller 22.

The vibration of the vibrated test object 21 is detected by a sensor 27 of an output vibration receiver 26 in a noncontact manner, and converted thereby into an electric signal, which is then processed by a signal conditioner 28. The sensor 27 may be of any of various known types for detecting vibrations, e.g., a displacement meter or the like. However, the sensor 27 should preferably have sharp directivity toward the test object 21 not to pick up ambient noise vibrations.

The signal conditioner 28 amplifies the electric signal from the sensor 27, and remove unnecessary high- and low-frequency components from the signal because the first-order energy peak of a fundamental natural vibration appears at 1.5 kHz and the second-order energy peak of a fundamental natural vibration appears at about 4 kHz which is about 2.5 times 1.5 kHz, as shown in FIG. 1A.

The electric signal from the output vibration receiver 26 is supplied through a transmission cable 29 to an arithmetic/decision system 30. The arithmetic/decision system 30 comprises a microcomputer, for example, that is programmed to effect various arithmetic and decision operations (described later). The software-implemented functions of the arithmetic/decision system 30 are shown in FIG. 7.

The supplied electric signal is applied to a gate 31 which extracts the natural-vibration component, depending on the shape of the test object 21, from the vibration of the test object 21 as represented by the electric signal, with a window W1 generated by a window generator 32. More specifically, when the test object is subjected to forced vibration the forced vibration produces an initial longitudinal wave which is mixed with the natural vibration. If a defect in the test object is a considerably large crack or cavity, then such a detect can be detected without being adversely affected by the mixed longitudinal wave. Usually, however, defects cannot be detected unless vibrations other than the natural vibration are removed as much as possible.

Removal of such other vibrations is effected in the apparatus shown in FIG. 7 as follows:

Two processes, i.e., the sine-wave process and the impulse process, are available for applying vibration to the test object 21. In the sine-wave process, vibration is applied to the test object 21 under certain conditions, and then the application of vibration is stopped at a certain instant. Upon elapse of a certain time after the stoppage of the application of vibration, the vibration of the test object 21 starts being measured. In the impulse process, the vibration of the test object 21 starts being measured upon elapse of a certain time after the test object 21 is vibrated by an impulsive impact.

The time which elapses before the vibration measurement after the application of vibration is stopped or the impact is applied, is determined as follows: The velocity c of a sound wave propagated in the test object 21 varies depending on the Young's modulus E (modulus of elasticity) and the density $\rho$ of the material of the test object 21, and is expressed by the following equation:

$$c = \sqrt{\frac{E}{\rho}}.$$

For example, if the test object 21 is in the form of a cast-iron cylinder and vibrated by the impulse process, then the velocity of the longitudinal wave in the test object 21 is 4560 m/s, and the velocity of the transverse wave in the test object 21 is 1/1.8 times the velocity of the longitudinal wave, i.e., about 2780 m/s. FIG. 9A shows a waveform in the time domain of the vibration of the test object 21 which is picked up immediately after the application of the impact. As shown in FIG. 9A, only the faster longitudinal wave continues for about 26 $\mu$sec., and thereafter the transverse wave is detected. After the peak of the transverse wave, the vibration is exponentially attenuated until it stops.

Since the vibration of the test object 21 is identical to the vibration caused by an earthquake, the vibration is composed of a mixture of faster and slower waves. Moreover, the forced vibration remains in the vibration of the test object 21. As a result, the waveform shown in FIG. 9A is not representative of the natural vibration inherent in the configuration of the test object 21. The waveform of the inherent natural vibration is considered to be observed slightly before the vibration stops, just like the "precession" of a spinning top. Therefore, the vibration of the test object 21 is extracted after it has started being attenuated past the peak of the transverse wave. The vibration of the test object 21 after the peak of the transverse wave is extracted using a rectangular extracting window W1 as shown in FIG. 9B.

The window W1 generated by the window generator 32 extracts the natural vibration inherent in the test object 21 from the vibration of the test object 21 in the gate 31 to which the electric signal is supplied from the output vibration receiver 26.

In FIG. 9B, the window W1 has a leading edge which rises 20 msec. after the impact is applied to the test object 21. The window W1 has a duration of 200 msec. The window generator 32 generates the window W1 based on a control signal from the controller 22 which indicates the start of the vibration of the test object 21.

The natural-vibration component thus extracted with the window W1 is then converted by an A/D converter 33 into digital data which is thereafter stored in a memory 34. The stored digital data is then read from the memory 34, and processed by a waveform emphasizer 35 with a waveform-emphasizing window W2 generated by another window generator 36. The window W2 is generated based on the control signal from the controller 22 which indicates the start of the vibration of the test object 21.

The window W2 will be described below. A vibration waveform produced by a small crack, cavity, blowhole, or other defect is apt to be included in the extracted natural-vibration waveform inherent with the test object 21, and can be detected relying upon the Q or sharpness of frequency selectivity. It may also be possible to reduce the width of the spreading portion of the spectral peak waveform of fundamental natural vibration for easier determination of a crack, blowhole, or the like. One approach is to correct the signal to sharply attenuate the signal amplitude below 50% of the peak (without varying the Q) as indicated by the broken lines 19 in FIG. 3 With the signal thus emphasized, the spreading portion of the spectra peak waveform is reduced in width, so that a spectral energy peak induced by a small defect in the test object 21 can be detected as being distinguished from the spectral energy peak of fundamental natural vibration, without relying on the Q.

To emphasize the spectral peak waveform, the signal from the memory 34 which is indicative of the extracted natural-vibration component is processed by the window W2 that is expressed by the following equation:

$$y = a\cos^2(x\omega t) + b\cos^2(x\omega t + \tau) + \ldots + k\cos^2(x\omega t + n\tau) + C$$

where $\tau$ is a time lag which may be $\lambda/4$ ($\lambda$ is the wavelength) and $a = b = \ldots = k$. The window W2 has a waveform as shown in FIG. 9C.

Figure 10A:
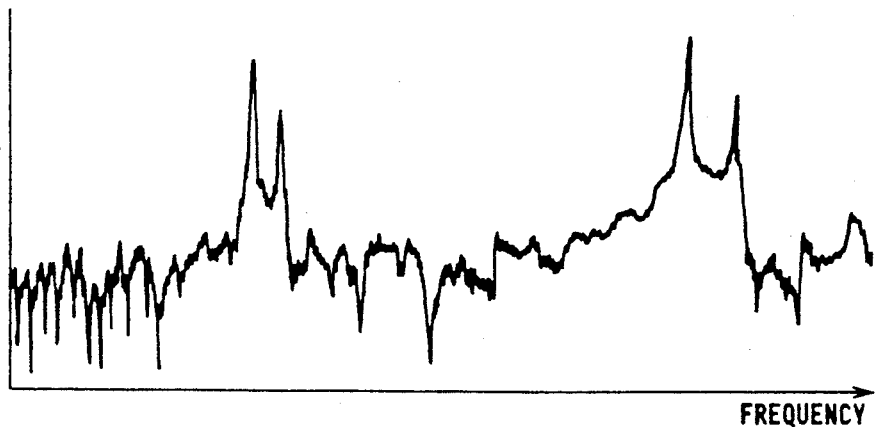
FIGS. 10A, 10B, and 10C are diagrams showing the waveforms of natural vibrations of the test object, after they are produced, after they are processed with the extracting window, and after they are processed with the emphasizing window.
Figure 10B:
Figure 10C:
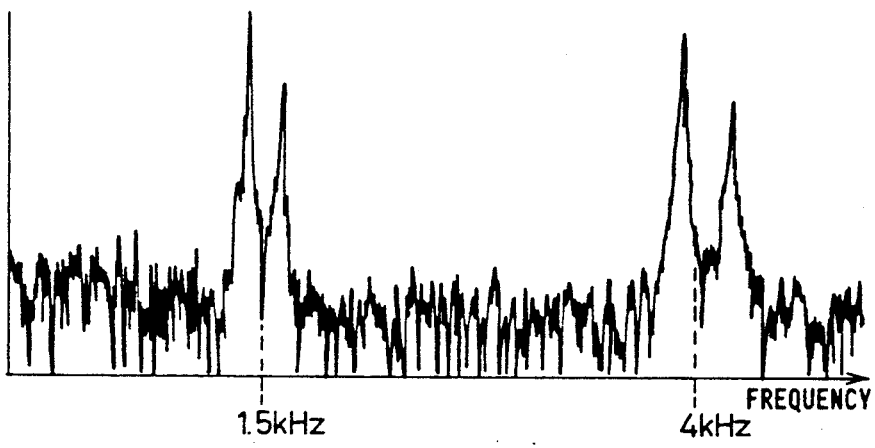

FIG. 10A shows a spectrum of the picked-up vibration of the test object 21 before being processed with the windows W1, W2. FIG. 10B shows a spectrum of the vibration which is extracted with the window W1 upon elapse of 20 msec. immediately after the test object 21 has started being vibrated. It can be seen from FIG. 10B that an energy peak of a fundamental natural vibration and a defect-induced energy peak are observed as being separated from each other. FIG. 10C shows a spectrum of the vibration which is emphasized with the window W2, indicating that the energy peak of fundamental natural vibration and the defect-induced energy peak are more clearly separated from each other.

The waveform-emphasized data is thereafter supplied to a spectrum analyzer 37 for spectral analysis.

Figure 11A:
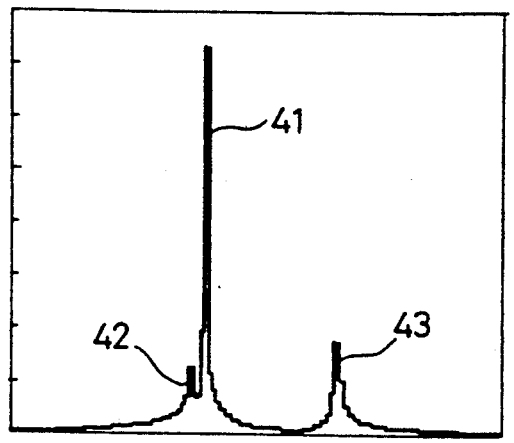
FIGS. 11A through 11C and 12A through 12C are diagrams illustrative of spectra energy peaks produced when the test object is vibrated in two positions.
Figure 11B:
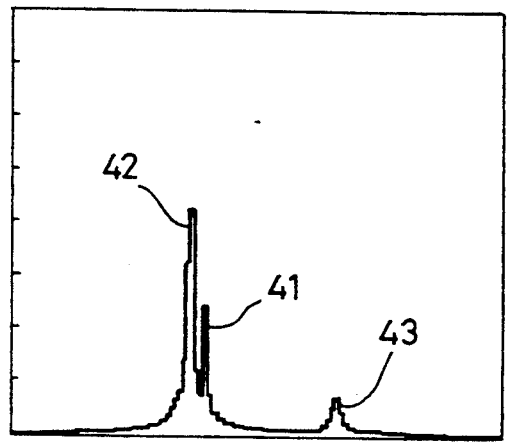
Figure 11C:
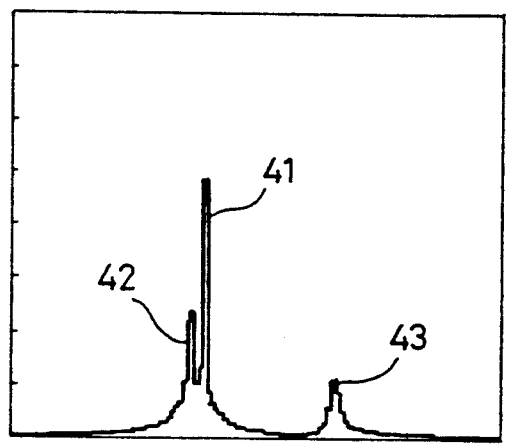

FIG. 11A shows a first-order spectral region of vibrations produced when the test object 21 is vibrated in the position P1. The first-order spectral region contains an energy peak 41 of a fundamental natural vibration of the upper portion of the test object 21, a defect-induced energy peak 42 which is paired with the energy peak 41, and an energy peak 43 of a fundamental natural vibration of the lower portion of the test object 21. The defect-induced energy peak 42 is relatively small, and it takes a long period of time to detect the energy peak 42 as it cannot easily be distinguished from signals due to material differences in the test object 21. According to the present invention, however, the test object 21 is also vibrated in the position P2 which is 22.5° apart from the position P1. FIG. 11B shows a first-order spectral region of vibrations produced when the test object 21 is vibrated in the position P2. As shown in FIG. 11B, a defect-induced energy peak 42 is of a greater amplitude than an energy peak 41 of a fundamental natural vibration. The spectral data shown in FIGS. 11A and 11B are combined into spectral data shown in FIG. 11C, which clearly indicates that a crack is present in the upper portion of the test object 21.

When the measuring stage 24 is further turned 22.5° and then the test object 21 is vibrated, a resultant first-order spectral region indicates that an energy peak of a fundamental natural vibration and a crack-induced energy peak depend on the vibrating position.

Figure 12A:
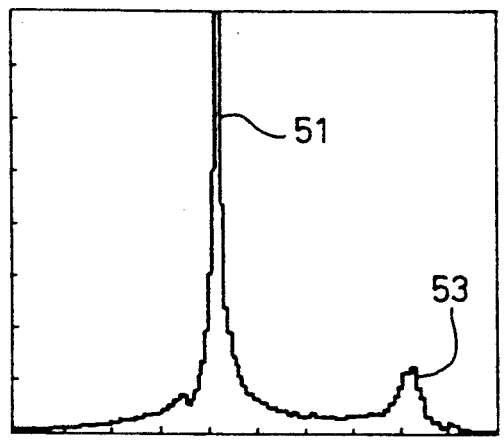

FIG. 12A shows a second order spectral region of vibrations produced when the test object 21 is vibrated in the position P1. The second-order spectral region contains an energy peak 51 of a fundamental natural vibration of the upper portion of the test object 21, and an energy peak 53 of a fundamental natural vibration of the lower portion of the test object 21. An energy peak produced by defect-induced vibration is included in the energy peak 51.

Figure 12B:
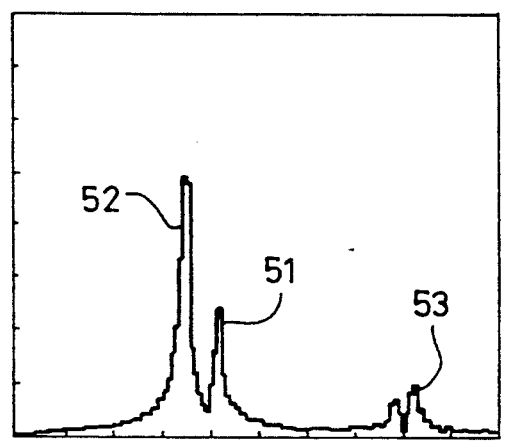
Figure 12C:
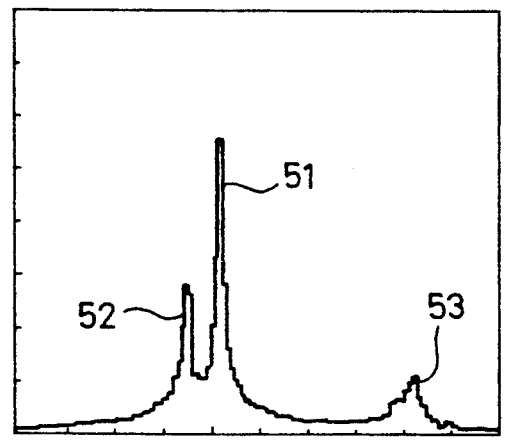

FIG. 12B shows a second-order spectral region of vibrations produced when the test object 21 is vibrated in the position P2. As shown in FIG. 12B, a defect-induced energy peak 52 appears which is of a greater amplitude than an energy peak 51 of a fundamental natural vibration. The spectral data shown in FIGS. 12A and 12B are combined into spectral data shown in FIG. 12C, which clearly indicates the defect-induced energy peak 52, i.e., that a trapped defect such as a cavity is present in the upper portion of the test object 21. Another defect-induced energy peak 54 appears which is paired with the energy peak 53, indicating that the trapped defect exists at an axially intermediate position in the test object 21.

When the measuring stage 24 is further turned 22.5° and the test object 21 is vibrated, a resultant second-order spectral region indicates that an energy peak of a fundamental natural vibration and a defect-induced energy peak depend on the vibrating position.

Using the combined spectral data, a defect determining unit 38 determines whether there is a defect-induced spectral energy peak or not, in the manner described below.

Figure 13:
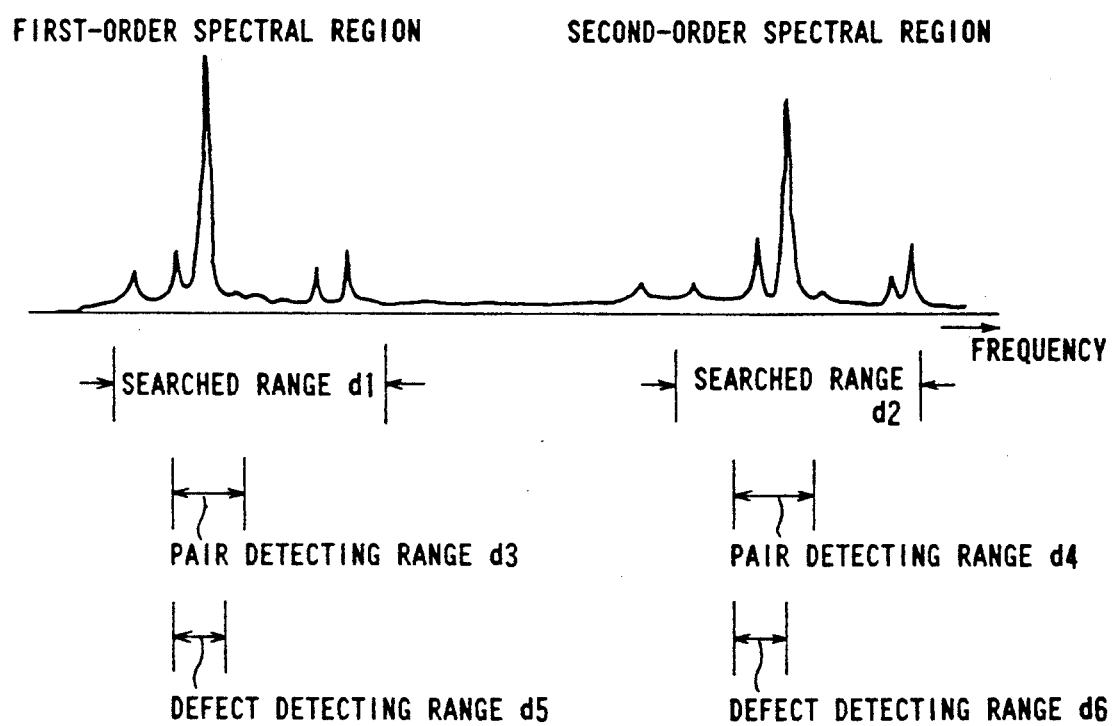
FIG. 13 is a diagram illustrative of the manner in which a defect is determined by a defect determining unit in the apparatus shown in FIG. 7.

As shown in FIG. 13, the defect determining unit 38 determines, from the spectrum, five energy peaks successively in order from the greatest amplitude in each of a first-order spectral frequency range d1 and a second-order spectral frequency range d2, and stores the values of the energy peaks and the frequencies thereof. Then, the defect determining unit 38 searches the stored frequencies for any pair of energy peaks whose frequencies fall within preset frequency ranges d3, d4 (d3, d4<d1, d2) with respect to both the first- and second-order spectral regions. These frequency ranges d3, d4 are determined in advance such that they will contain a pair of energy peaks of a fundamental natural vibration and an energy peak of vibration induced by a defect such as a crack, a blowhole, a cavity, or the like. If such a pair is detected within the frequency range d3 in the first-order spectral region, the defect determining unit 38 determines the higher frequency of a lower-frequency pair as the position of a first-order energy peak of a fundamental natural vibration. The defect determining unit 38 then determines whether there is an energy peak (which may be a pair of energy peaks) other than the determined energy peak of a fundamental natural vibration, within a preset frequency range d5 that is narrower than the frequency range d3. If there is an energy peak within the frequency range d5, the defect determining unit 38 determines that there is a crack in the test object 21.

If a pair of energy peaks is detected within the frequency range d4 in the second-order spectral region, then the defect determining unit 38 determines the higher frequency of a lower-frequency pair as the position of a second-order energy peak of a fundamental natural vibration. The defect determining unit 38 then determines whether there is an energy peak other than the determined energy peak of a fundamental natural vibration, within a preset frequency range d6 that is narrower than the frequency range d4. If there is an energy peak within the frequency range d6, the defect determining unit 38 determines that there is a blowhole or cavity in the test object 21.

Figure 14:
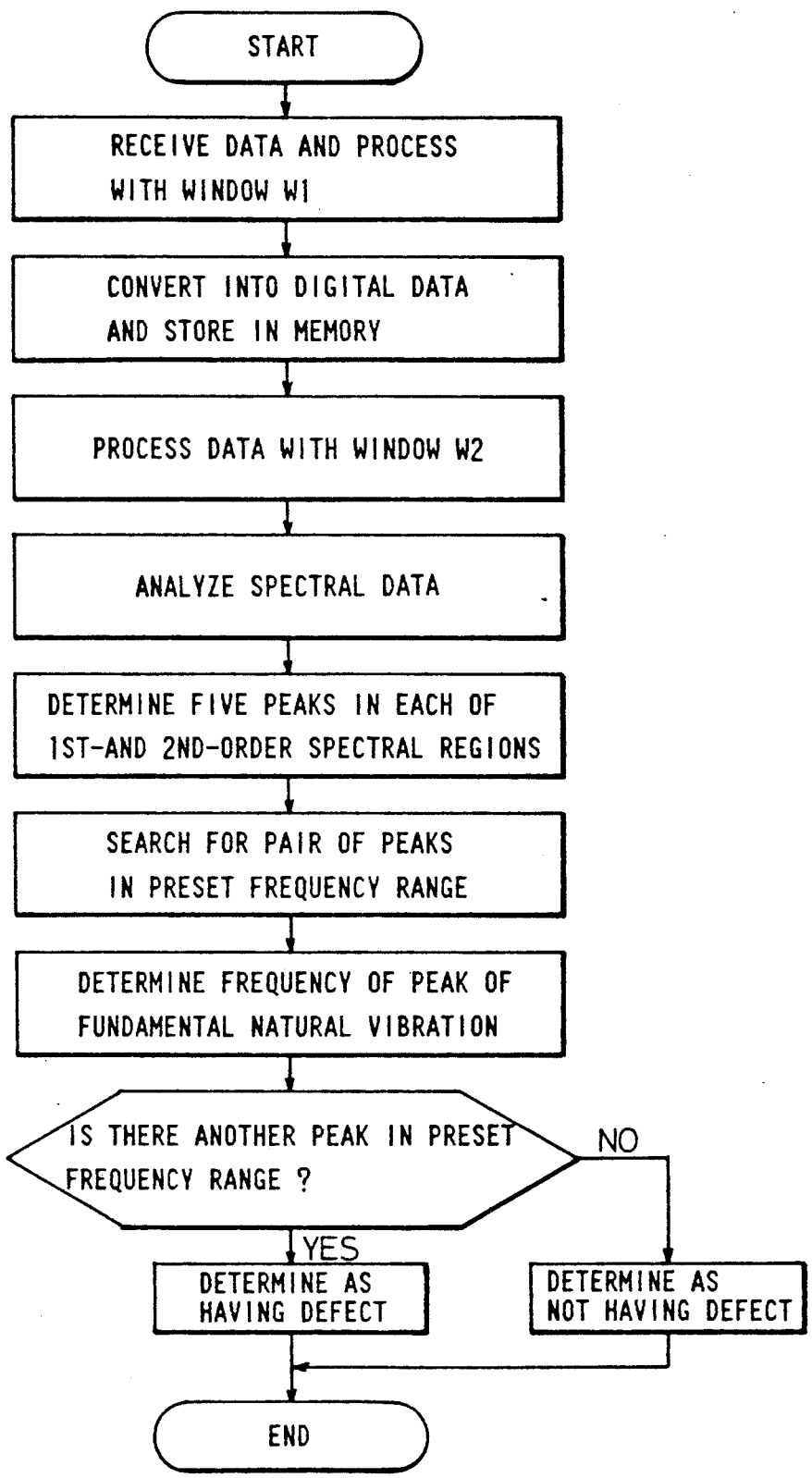
FIG. 14 is a flowchart of an operation sequence of the apparatus shown in FIG. 7.

The above operation sequence of the arithmetic/decision system 30 is shown in the flowchart of FIG. 14.

If it is determined by the defect determining unit 38 that the test object 21 has a crack (through defect) or a blowhole or cavity (trapped defect), the position determining unit 39 determines the position of the defect.

More specifically, based on either the energy peaks of a fundamental natural vibration or the energy peaks of a defect-induced vibration produced when the test object 21 is vibrated in the positions P1 through P3, the position determining unit 39 estimates and plots the loci of energy peaks in the first- and second-order spectral regions along the circumference of the cylindrical test object 21, as shown in FIGS. 4 and 6. The position determining unit 39 then determines, from the plotted loci, four 90°-spaced positions where a crack may possibly be present, and six 60°-spaced positions where a blowhole or cavity may possibly be present.

Since the positions P1 through P3 are already known, an angle by which one position where a defect may possibly be present is angularly displaced from the position P3, for example, is determined, and the measuring stage 24 is turned by the determined angle. Then, a corresponding portion of the test object 21 is marked with a paint by a marker applicator (not shown). To mark all four or six positions where a defect may possibly exist, the measuring stage 24 is successively turned through 90° or 60° from the marked position, and portions of the test object 21 which correspond to those positions are marked. At this time, the positions where a crack (through defect) may possibly exist and the positions where a trapped defect ma possibly exist may be marked in different marker colors so that they can be distinguished from each other.

In the above embodiment, the test object 21 is vibrated at a relatively small number of positions for determining positions where a defect may possibly be present. However, it is also possible to apply vibration to the test object 21 in successively angularly spaced positions along the fully circumference of the test object 21 for the determination of positions where a defect may possibly be present. More specifically, based on the energy peaks of a fundamental natural vibration and the energy peaks of a defect-induced vibration produced when the test object 21 is vibrated in those successively angularly spaced positions around the circumference of the test object 21, the position determining unit 39 determines the loci of those energy peaks in the first- and second-order spectra regions. Then, the position determining unit 39 determines, from the determined loci, a position where the difference between the energy peaks of a fundamental natural vibration and defect-induced vibration is maximum, and determines that position as a defect position.

Whether the defect is in the upper or lower portion of the test object 21 can also be determined by checking if the defect-induced energy peak is paired with an energy peak of a fundamental natural vibration at a lower frequency or a higher frequency, as described above.

A test object, i.e., an inspected product, which is determined as having a defect is rejected as a defective product from the production line by a sorter 40. An inspected product which is determined as having no defects is fed to a next process. In this manner, all products are successively inspected for defects.

As described above, the apparatus according to the present invention can detect whether a test object has a defect or not, reliably and in a short period of time, based on first- and second-order spectral energy peaks of vibration produced when the test object is vibrated at a plurality of positions.

In addition, the apparatus can also determine whether a defect is in the upper or lower portion of the test object, by applying vibration to the test object at a position off the center of gravity thereof.

In the illustrated example, the test object is vibrated at three positions which are 22.5° spaced apart. However, the test object may be vibrated at other angular positions except those corresponding to 90°, 180°, 270°. For example, the test object may be vibrated at three 45°-spaced positions. FIGS. 15A through 15C and 16A through 16C show energy peaks in first- and second-order spectral regions when the test object 21 is vibrated at two 45°-spaced positions on its upper portion.

Figure 15A:
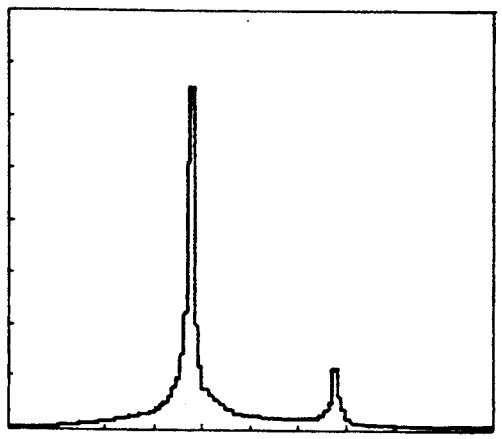
FIGS. 15A through 15C and 16A through 16C are diagrams illustrative of spectral energy peaks produced when the test object is vibrated in other positions.
Figure 15B:
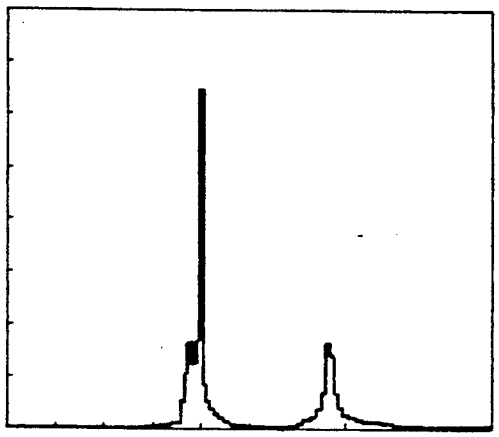
Figure 15C:
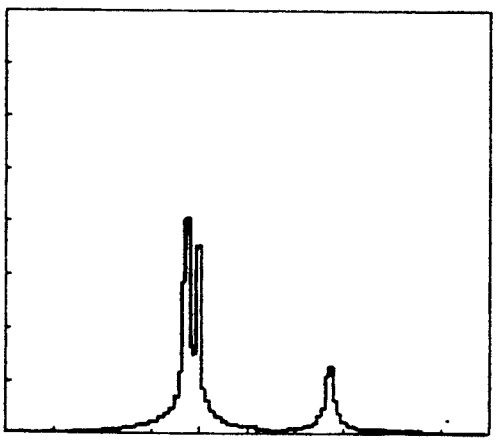

FIG. 15A shows vibrations of the test object in a first-order spectral region when it is vibrated at the first position. In FIG. 15A, an energy peak of a defect-induced vibration is so large that it includes an energy peak of a fundamental natural vibration. Therefore, these energy peaks cannot be recognized as a pair, and the energy peak of a defect-induced vibration cannot be distinguished from an energy peak due to a material difference in the test object. FIG. 15B shows vibrations of the test object when it is vibrated at the second position. The spectral region shown in FIG. 15B indicates an energy peak of a fundamental natural vibration. When the spectral data shown in FIGS. 15A and 15B are combined into spectral data shown in FIG. 15C, the energy peaks of a fundamental natural vibration and defect-induced vibration can clearly be recognized as a pair.

Figure 16A:
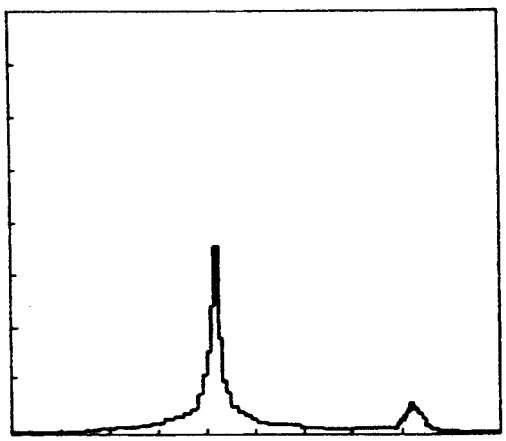
Figure 16B:
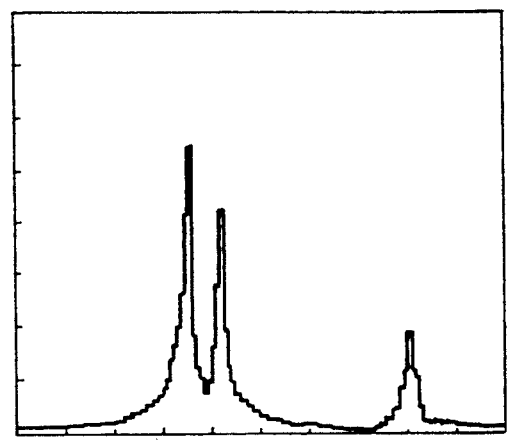
Figure 16C:
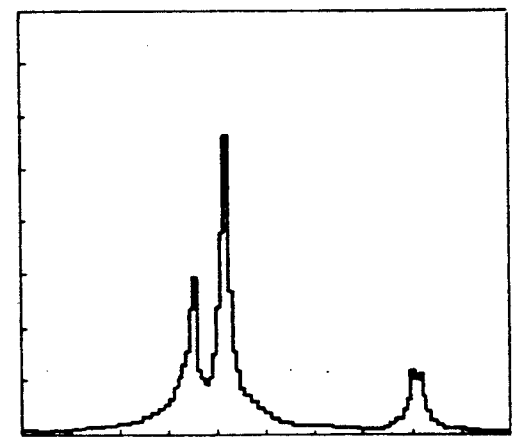

Likewise, a trapped defect in the test object can also clearly be recognized in spectra data shown in FIG. 16C which is a combination of spectral data shown in FIGS. 16A and 16B, that are produced in a second-order spectral region when the test object is vibrated at two positions. It can be determined from the spectral data shown in FIG. 16C that the trapped defect, which may be a cavity or blowhole, is located in the lower portion of the test object.

In the apparatus shown in FIG. 7, the arithmetic/-decision system 30 analyzes spectral data in the first- and second-order spectral regions, and detects a defect when there are two separate energy peaks in either the first- or second-order spectral regions. However, even if there are no separate energy peaks in the first and second order spectral regions, the arithmetic/decision system 30 may measure the magnitude of Q of the spectral data and detect a defect when the magnitude of Q is greater than a value which is produced when there is n defect in the test object. The apparatus thus modified can detect a defect with an increased degree of accuracy.

Rather than analyzing spectral data, the vibration waveform data stored in the memory may be converted into time-series data, the envelope of the data may be detected, and peaks of the envelope may be counted for the detection of a crack.

The test object 21 has been described as cylindrical in shape. However, the test object 21 may be of other cross-sectional shape, or may be in the form of a hexahedron or any of other polyhedrons, or a sphere. Furthermore, the test object 21 may be of any of various materials.

In the illustrated embodiment, the test object 21 is vibrated successively at the first position P1, the second position P2, the third position P3, and so on while turning the measuring stage 24 through successive angles. However, the measuring stage 24 may not be turned, but the test object 21 may be vibrated at the two positions P1, P2 by a plurality of weights.

The test object 21 may be vibrated at four or more positions, and according to any of various processes other than the impulse process.

With the present invention, as described above, since the test object is vibrated and the natural vibration thereof is detected by the sensor in a noncontact fashion, the waveform of the vibration is simple and easy to determine as it is not adversely affected by irregular reflections which would otherwise be caused if the sensor were held in contact with the test object through inadequate coupling. Therefore, it can be determined whether the test object has a defect therein or not, through stable measurements without disturbance. Moreover, the detection of a defect in the test object can be effected in a short period of time since the detecting process and the data used thereby are relatively simple.

Even if the test object has wrinkles or surface irregularities, any defect such as a crack, a blowhole, a cavity, a recess, or the like in the test object can reliably be detected provided defect-induced vibrations can be distinguished from the natural vibration.

Since the test object is vibrated at least two positions except those positions which are spaced by $90° \times n$, a defect-induced spectral energy peak can clearly be detected in a short period of time. If the test object were vibrated at only one position, it would take a long period of time to distinguish a defect-induced spectral energy peak from a spectral energy peak caused by a material difference in the test object.

The position of a defect in the entire test object, but not in a portion of the test object, can be determined simply by vibrating the test object.

Although a certain preferred embodiment has been shown and described, it should be understood that many changes and modifications may be made therein without departing from the scope of the appended claims.

What is claimed is:

1. A method of detecting a defect in a test object, comprising the steps of:
    (a) applying vibration to a three-dimensional test object at two positions on a side thereof to vibrate the test object;
    (b) generating a signal representing actual vibrations of the test object;
    (c) converting the signal generated in said step (b) to energy peak data indicative of a natural vibration of the test object and indicative of a defect-induced vibration of the test object when the test object is vibrated at two positions; and
    (d) comparing energy peaks indicative of a natural vibration and energy peaks indicative of a defect-induced vibration to determine whether a defect is present in the test object.

2. The method according to claim 1, wherein the positions are angularly spaced from each other by an angular interval other than 90° or an integer multiple of 90°.

3. The method according to claim 2, wherein the vibration is applied to the test object at different times at the two positions.

4. The method according to claim 2, wherein said step (d) comprises the sub-steps of:
    (d1) detecting a spectral energy peak of a natural vibration of the test object;
    (d2) detecting a spectral energy peak of a defect-induced vibration of the test object; and
    (d3) determining that there is a defect in the test object when the spectral energy peak of the defect-induced vibration is detected.

5. The method according to claim 4, wherein said step (d) comprises the sub-step of:
    (d4) combining first-order or second-order spectral data produced when the test object is vibrated at the two positions;
    said step (d3) determining that a defect is in the test object when a spectral energy peak other than the spectral energy peak of the natural vibration of the test object is present in the combined spectral data.

6. The method according to claim 5, wherein said step (d) comprises the sub-steps of:
    (d5) establishing a frequency range with respect to the first-order and second-order spectral data;
    (d6) detecting a plurality of spectral energy peaks in order from a largest amplitude within the frequency range;

(d7) determining whether frequencies of the detected spectral energy peaks fall in a detection range defined by a natural frequency of the test object and defect-induced frequency; and (d8) determining, when at least two spectral energy peaks are in the detection range, that one of the spectral energy peaks is caused by the natural vibration of the test object and the other spectral energy peak is caused by the vibration induced by a defect in the test object;

said step (d3) determining that a defect is in the test object based on the other spectral energy peak.

7. The method according to claim 6, wherein said step (d) comprises the sub-step of:

(d9) setting a frequency range with one of the spectral energy peaks at a center, the one of the spectral energy peaks being caused by the natural vibration of the test object;

said step (d3) determining any spectral energy peak in the frequency range established in said step (d9) as being caused by a defect in the test object.

8. The method according to claim 4, further comprising the steps of:

(e) selecting a plurality of positions where vibration is to be applied to the test object with respect to a center of gravity of the test object; and (f) determining a position of a defect in the test object based on the natural frequency of the test object and a frequency induced by the defect when the test object is vibrated at the selected positions.

9. The method according to claim 8, wherein the positions are located in either above or below the center of gravity of the test object and further comprising the step of:

(d6) determining whether a spectral energy peak of a defect-induced vibration of the test object is paired with a higher-frequency or a lower-frequency spectral energy peak of a natural vibration of the test object, thereby determining whether the defect is positioned above or below the center of gravity of the test object when the natural vibration of the test object vibrated in any one of the positions is subjected to a spectral analysis.

10. The method according to claim 1, wherein said step (d) comprises the sub-steps of:

(d1) determining a first spectral energy peak of a fundamental natural vibration of the test object from the signal indicative of the natural vibration of the test object;

(d2) determining a second spectral energy peak of a defect-induced vibration of the test object from the signal indicative of the defect-induced vibration of the test object; and (d3) determining, from the first and second spectral energy peaks produced when the test object is vibrated at the two positions, a position where a difference between the first and second spectral energy peaks is a maximum, the maximum difference representing a defect.

11. The method according to claim 10, wherein said step (d) comprises the sub-step of:

(d4) determining the difference between the first and second spectral energy peaks from a locus of the spectral energy peaks of the fundamental natural vibrations of the test object and a locus of the spectral energy peaks of the defect-induced vibration.

12. The method according to claim 11, wherein said step (d) comprises the sub-step of:

(d5) determining a waveform representing the locus of the spectral energy peaks of the defect-induced vibration of the test object;

said step (d3) determining that a defect is present from an area occupied by the waveform.

13. The method according to claim 10, wherein said step (d) comprises the sub-steps of:

(d4) establishing a frequency range with respect to first-order and second-order spectral data;

(d5) detecting a plurality of spectral energy peaks in order from a largest amplitude within the frequency range;

(d6) determining whether frequencies of the detected spectral energy peaks fall in a detection range defined by a natural frequency of the test object and a defect-induced frequency; and (d7) determining, when two spectral energy peaks are in the detection range, that one of the spectral energy peaks is caused by the natural vibration of the test object and the other spectral energy peak is caused by the vibration induced by a defect in the test object;

said step (d3) determining that a defect is the test object based on the other spectral energy peak.

14. The method according to claim 13, wherein said step (d) comprises the sub-step of:

(d8) setting a frequency range with one of the spectral energy peaks at a center, the one of the spectral energy peaks being caused by the natural vibration of the test object;

said step (d3) determining any spectral energy peak in the frequency range established in said step (d8) as being caused by a defect in the test object.

15. The method according to claim 10, further comprising the steps of:

(e) selecting a plurality of positions where vibration is to be applied to the test object with respect to a center of gravity of the test object; and (f) determining a position of a defect in the test object based on a natural frequency of the test object and a frequency induced by the defect when the test object is vibrated in the selected positions.

16. The method according to claim 15, wherein the positions are located either above or below the center of gravity of the test object and further comprising the step of:

(d6) determining whether a spectral energy peak of a defect-induced vibration of the test object is paired with a higher-frequency or a lower-frequency spectral energy peak of a natural vibration of the test object, thereby determining whether the defect is positioned above or below the center of gravity of the test object when the natural vibration of the test object vibrated at any one of the positions is subjected to a spectral analysis.

17. The method according to claim 1, wherein the test object is of a circular or elliptical cross-sectional shape and further comprising the steps of:

(e) applying vibration to the test object at three positions along a surface of the cross-sectional shape, the positions being angularly spaced by an angular interval of less than 90°/3 and other than 60° or an integer multiple of 60° when even-numbered-order spectral data are to be measured;

(f) detecting vibration of the test object when the test object is vibrated at the three positions;

(g) detecting spectral energy peaks of a fundamental natural vibration of the test object and spectral energy peaks of a defect-induced vibration of the test object from the detected vibration; and (h) determining a position where a defect may possibly exist in the test object from a locus of spectral energy peaks.

18. The method according to claim 1, wherein the test object is of a circular or elliptical cross-sectional shape and further comprising the steps of:

(e) applying vibration to the test object at positions along a surface of the cross-sectional shape and off a center of gravity of the test object; and (f) determining whether a spectral energy peak of a defect-induced vibration of the test object is paired with a higher-frequency or a lower-frequency spectral energy peak of a natural vibration of the test object, thereby determining whether the defect is positioned above or below the center of gravity of the test object when the natural vibration of the test object vibrated at any one of the positions is subjected to a spectral analysis.

19. The method according to any one of claims 1 through 18, further comprising the steps of:

(y) detecting a spectral energy peak of a transverse wave produced after the test object is vibrated; and (z) detecting a natural frequency of the test object and frequency of a vibration induced by a defect in the test object from the spectral energy peak of the transverse wave.

20. An apparatus for detecting a defect in a test object, comprising:

vibrating means for vibrating a test object in a plurality of positions;

detecting means for detecting vibration of the test object and converting the detected vibration into an electric signal; and determining means for determining whether there is a defect in the test object according to energy peaks in the electric signal from said detecting means which is indicative of a natural vibration of the test object and of a defect-induced vibration of the test object.

21. The apparatus according to claim 20, further comprising:

a rotatable measuring stage for supporting the test object thereon;

said rotatable measuring stage having an elastic member.

22. The apparatus according to claim 20, wherein said determining means comprises:

gate means for introducing, at a predetermined time interval, said signal indicative of the natural vibration of the test object the defect-induced vibration of the test object;

memory means for storing a signal outputted from said gate means as spectral data;

spectrum analysis means, operatively connected to an output terminal of said memory means, for processing spectral data corresponding to the natural vibration of the test object and spectral data corresponding to the defect-induced vibration of the test object; and defect determining means, operatively connected to an output terminal of said spectrum analyzing means, for determining whether a defect is in the test object based on the processed spectral data.

23. The apparatus according to claim 22, further comprising:

position determining means, operatively connected to an output terminal of said defect determining means, for determining a position of a defect in the test object.

24. The apparatus according to claim 23, wherein said position determining means comprises:

first means, responsive to said electric signal from said detecting means, for determining first spectral energy peaks of a fundamental natural vibration of the test object and second spectral energy peaks of the defect-induced vibration of the test object by analyzing a spectrum of the natural vibration of the test object which is vibrated at said plurality of positions;

second means for determining a locus of the first spectral energy peaks of the fundamental natural vibration of the test object and a locus of the second spectral energy peaks of the defect-induced vibration of the test object; and third means for detecting a position where a difference between the first and second spectral energy peaks is a maximum from said loci and for determining said position with the maximum difference as containing a defect.

* * * * *